(12) United States Patent
Schachtner et al.

(10) Patent No.: US 9,970,983 B2
(45) Date of Patent: May 15, 2018

(54) METHODS AND DEVICES FOR THE COMPUTER-AIDED DETERMINATION OF DEVIATION PATTERNS DURING THE PRODUCTION AND/OR TESTING OF A MULTIPLICITY OF DIES AND COMPUTER PROGRAM PRODUCTS

(71) Applicant: Infineon Technologies AG, Neubiberg (DE)

(72) Inventors: Reinhard Schachtner, Undorf (DE); Gerhard Poeppel, Duggendorf (DE)

(73) Assignee: Infineon Technologies AG, Neubiberg (DE)

( * ) Notice: Subject to any disclaimer, the term of this patent is extended or adjusted under 35 U.S.C. 154(b) by 458 days.

(21) Appl. No.: 14/612,343

(22) Filed: Feb. 3, 2015

(65) Prior Publication Data
US 2015/0219715 A1 Aug. 6, 2015

(30) Foreign Application Priority Data
Feb. 3, 2014 (DE) .................. 10 2014 101 289

(51) Int. Cl.
*G01R 31/28* (2006.01)
*G01R 31/26* (2014.01)
(Continued)

(52) U.S. Cl.
CPC ..... *G01R 31/2834* (2013.01); *G01R 31/2601* (2013.01); *G01R 31/2894* (2013.01);
(Continued)

(58) Field of Classification Search
CPC ............ G01R 31/2834; G01R 31/2601; G01R 31/2894; G01R 31/3185; G01R 31/31707;
(Continued)

(56) References Cited

U.S. PATENT DOCUMENTS

| | | | |
|---|---|---|---|
| 5,497,381 A * | 3/1996 | O'Donoghue | H01L 22/20 257/E21.525 |
| 6,393,602 B1 * | 5/2002 | Atchison | H01L 22/20 257/E21.525 |
| 2002/0156550 A1 * | 10/2002 | Langford | G01R 31/2831 700/110 |

OTHER PUBLICATIONS

Schachtner, R. et al., "A Nonnegative Blind Source Separation Model for Binary Test Data", IEEE Transactions on Circuits and Systems I: Regular Papers, vol. 57, Jul. 2010, No. 7, p. 1439-1448.
(Continued)

*Primary Examiner* — Ajay Ojha
(74) *Attorney, Agent, or Firm* — Viering, Jentschura & Partner mbB

(57) ABSTRACT

In various embodiments, a method for the computer-aided determination of deviation patterns during at least one of the production or testing of a multiplicity of dies is provided. The dies are uniquely identified. The method may include determining, for each die of the multiplicity of dies and for at least one measurement process of a plurality of measurement processes which are applied to at least one portion of the dies, a measurement value which was determined in the measurement process for the respective die; and carrying out a blind source separation using the measurement values, thereby determining the deviation patterns for the dies.

22 Claims, 8 Drawing Sheets

(51) Int. Cl.
  *G01R 31/3185* (2006.01)
  *H01L 21/66* (2006.01)
  *G01N 21/95* (2006.01)
  *G01R 31/317* (2006.01)

(52) U.S. Cl.
  CPC ...... *G01N 21/9501* (2013.01); *G01R 31/3185* (2013.01); *G01R 31/31707* (2013.01); *G06T 2207/30148* (2013.01); *H01L 22/20* (2013.01); *H01L 22/34* (2013.01)

(58) Field of Classification Search
  CPC .................... H01L 22/34; H01L 22/20; G06T 2207/30148; G01N 21/9501
  See application file for complete search history.

(56) References Cited

OTHER PUBLICATIONS

Schachtner, R., "Extensions of Non-negative Matrix Factorization and their Application to the Analysis of Wafer Test Data", Dissertation, Feb. 2010, 156 pages, University of Regensburg, Germany.

\* cited by examiner

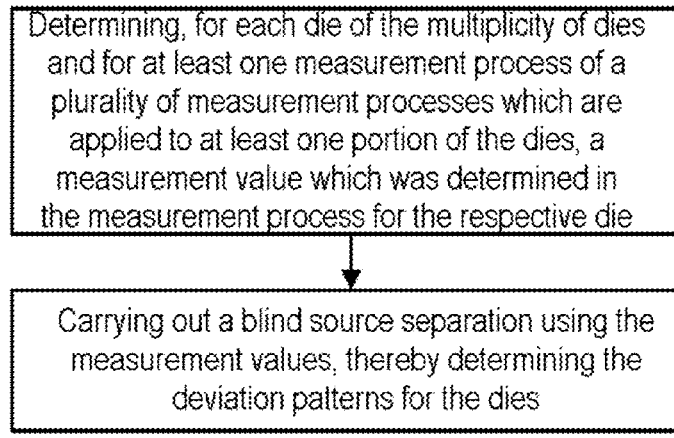
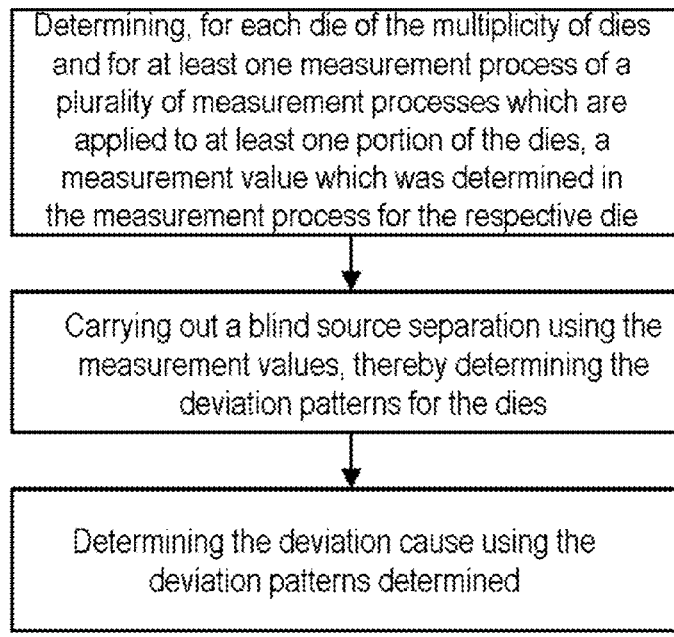

FIG 9

802: Forming a data tensor comprising: in a first dimension, referenced by means of a first index i, and/or a second dimension, referenced by means of a second index j, an identification indication for uniquely identifying each die; and in a third dimension, referenced by means of a third index t, an identification indication for identifying a measurement process of a purality of different measurement processes to which the dies are subjected, wherein a value ($X_{ijt}$) in the data tensor represents a measurement value which is assigned to the respective die ij and which was determined in the measurement process t. The method furthermore comprise

804: Carrying out a blind source separation on the basis of the data tensor, thereby determining the deviation patterns for the dies

902: Determining the deviation cause using the deviation patterns determined

METHODS AND DEVICES FOR THE COMPUTER-AIDED DETERMINATION OF DEVIATION PATTERNS DURING THE PRODUCTION AND/OR TESTING OF A MULTIPLICITY OF DIES AND COMPUTER PROGRAM PRODUCTS

CROSS-REFERENCE TO RELATED APPLICATION

This application claims priority to German Patent Application Serial No. 10 2014 101 289.5, which was filed Feb. 3, 2014, and is incorporated herein by reference in its entirety.

TECHNICAL FIELD

Various embodiments relate generally to methods and devices for the computer-aided determination of deviation patterns during the production and/or testing of a multiplicity of dies and computer program products.

BACKGROUND

During the production of a multiplicity of chips, attempts are often made to deduce deviation patterns from test results of tested chips in a computer-aided manner, from which deviation patterns possible deviation causes in the production process can subsequently be inferred.

In this context, a method of so-called blind source separation is conventionally used, in which a matrix factorization is carried out by a maximum likelihood optimization method. However, this method takes into account only for exactly one test whether or not a chip has passed this test.

In practice, however, a plurality of tests or measurements are carried out, which cannot be taken into account in the context of the conventional maximum likelihood optimization method.

SUMMARY

In various embodiments, a method for the computer-aided determination of deviation patterns during at least one of the production or testing of a multiplicity of dies is provided. The dies are uniquely identified. The method may include determining, for each die of the multiplicity of dies and for at least one measurement process of a plurality of measurement processes which are applied to at least one portion of the dies, a measurement value which was determined in the measurement process for the respective die; and carrying out a blind source separation using the measurement values, thereby determining the deviation patterns for the dies.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 6 shows a flow diagram illustrating a method for the computer-aided determination of deviation patterns during the production and/or testing of a multiplicity of dies, wherein the dies are uniquely identified;

FIG. 7 shows a flow diagram illustrating a method for the computer-aided determination of at least one fault cause of faults during the production and/or testing of a multiplicity of dies, wherein the dies are uniquely identified;

FIG. 9 shows a flow diagram illustrating a method for the computer-aided determination of at least one fault cause of faults during the production and/or testing of a multiplicity of dies, wherein the dies are uniquely identified.

DESCRIPTION

Figure 1:
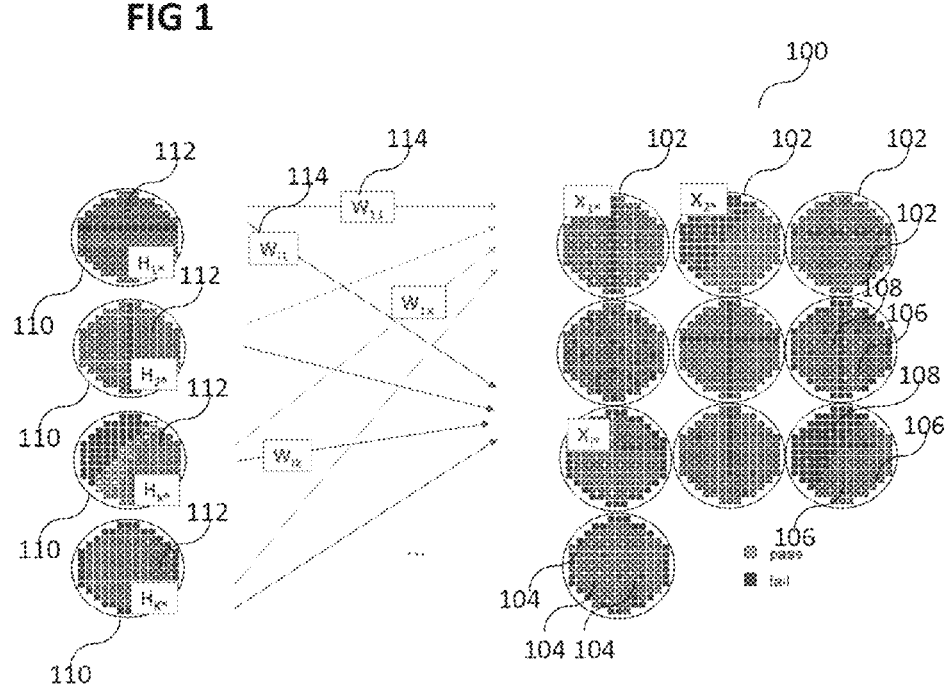
FIG. 1 shows an illustration for elucidating a blind data separation in accordance with various embodiments.

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

The word "over" used with regards to a deposited material formed "over" a side or surface, may be used herein to mean that the deposited material may be formed "directly on", e.g. in direct contact with, the implied side or surface. The word "over" used with regards to a deposited material formed "over" a side or surface, may be used herein to mean that the deposited material may be formed "indirectly on" the implied side or surface with one or more additional layers being arranged between the implied side or surface and the deposited material.

In the following detailed description, reference is made to the accompanying drawings, which form part of this description and show for illustration purposes specific embodiments in which the invention can be implemented. In this regard, direction terminology such as, for instance, "at the top", "at the bottom", "at the front", "at the back", "front", "rear", etc. is used with respect to the orientation of the figure(s) described. Since component parts of embodiments can be positioned in a number of different orientations, the direction terminology serves for illustration and is not restrictive in any way whatsoever. It goes without saying that other embodiments can be used and structural or logical changes can be made, without departing from the scope of protection of the present invention. It goes without saying that the features of the various embodiments described herein can be combined with one another, unless specifically indicated otherwise. Therefore, the following detailed description should not be interpreted in a restrictive sense, and the scope of protection of the present invention is defined by the appended claims.

In the context of this description, the terms "connected" and "coupled" are used to describe both a direct and an indirect connection and a direct or indirect coupling. In the figures, identical or similar elements are provided with identical reference signs, in so far as this is expedient.

Various embodiments improve deviation patterns determined in a computer-aided manner, said deviation patterns describing deviations during the production and/or during the testing of dies, and thus also simplify a possible deviation analysis, for example fault analysis, or a search for a cause of the deviation, for example a fault-finding search, and possibly also make it more reliable and more exact.

In the context of this description, a die may be understood to mean a structure on a wafer which can contain both a chip and so-called sawing frame regions surrounding said chip. Consequently, the method may for example also be applied to test structures contained in one or more sawing frames, such as PCM test structures (process control monitoring test structures), for example, or these can be taken into account jointly with chip test results. However, the term die is also intended to encompass singulated chips or ensembles of chips, which if appropriate can even already be at least partly packaged.

In this regard, the measurements or tests can relate to measurements or tests which are carried out on as yet unsingulated dies in one or a plurality of front end of line process(es) and/or are carried out in one or a plurality of back end of line process(es).

During the production of dies or chips, generally during the processing of wafers or already singulated chips (for example during the packaging of chips), a multiplicity of different influences which lead to a deviation can occur, for example harmful influences (hereinafter only harmful influences are described concretely, but it should be pointed out that the embodiments, without any restriction of general validity, are applicable to all influences which lead to a deviation which can be determined in a deviation pattern), said influences causing damage (possibly even destruction) of one or a plurality of dies or one or a plurality of chips. This damage can occur on a wafer or, for example, during the packaging of a possibly already singulated chip or during the packaging of a plurality of chips such as, for example, in the case of a wafer level package (wafer level packaging).

Examples of possible harmful influences are (without any restriction of general validity; the various embodiments are in no way restricted to specific harmful influences and can determine references to inherently arbitrary harmful influences):
 a faulty process or a plurality of faulty processes in the front end of line, for example a faulty lithography process, etching process, doping process, or the like;
 a faulty process or a plurality of faulty processes in the back end of line, for example a faulty chip individualization process (chip singulation process, for example sawing process or etching process or breaking process), etching process, doping process, or the like;
 a faulty measurement process or a plurality of faulty measurement processes or a faulty test process or a plurality of faulty test processes, or the like; or
 faulty design revealed by process or test variation, or the like.

Furthermore, the dies or chips are subjected to a multiplicity of different measurement processes and/or test processes.

The recorded measurement data (also designated as measurement values) and/or test data (also designated as test results) may be incomplete since, in various embodiments, provision may be made, for example in accordance with the so-called "stop-at-first-fail" procedure, for not measuring or testing a die or a chip any further if the die or chip has not passed a test or, in a measurement process, the measurement values determined for a die or a chip were so poor, i.e. deviated from setpoint values to such an extent, that further processing or measurement or testing no longer appears to be expedient for the die or chip.

The measurement data and/or test data determined result from a superposition, to put it another way a (e.g. additive) combination of the different harmful influences (also designated as damage causes), wherein each harmful influence has a different degree of influence (also designated as activation degree) on each wafer, possibly even on each die or chip. Each die or chip of a wafer can furthermore "fail" in different tests, to put it another way not pass different tests, wherein, as was described above, possibly only the first test not passed is recorded for a die or chip.

It is desirable, without initially having knowledge of harmful influences actually present, to determine only from the measurement data and/or test data deviation patterns (for example fault patterns) which enable a reliable reference to harmful influences possibly present, said reference for example also being processable in an automated manner (in a computer-aided manner), in order finally to determine and, if appropriate, eliminate the harmful influences actually present.

For this purpose, as explained in even greater detail below, a method of so-called blind source separation is used, which in various embodiments illustratively is based on a tensor factorization with missing tensor values, i.e. missing measurement values and/or test data in the tensor.

Illustratively, in various embodiments, the determined measurement data and/or test data are decomposed into different data structures, for example matrices and tensors.

In various embodiments, a die or chip is uniquely identified, for example by an identification indication assigned to the die or chip. In this regard, a die or chip can be assigned a first index i (which can also reference a first dimension in a data tensor), which identifies for example a wafer (or for example an auxiliary carrier in the case of an eWLP method) on which the die or chip is arranged. Furthermore, alternatively or additionally, a die or chip can be assigned a second index j (which can also reference a second dimension in a data tensor), which identifies for example the chip j on the wafer i (or for example on the auxiliary carrier in the case of a wafer level package method). Finally, in various embodiments, the die or chip can be assigned a third index t (which can also reference a third dimension in a data tensor), which can represent an identification indication for identifying a measurement process of a plurality of different measurement processes (for example a test process of a plurality of different test processes) to which the dies are subjected. It is possible, of course, if desired, to provide further identification information and thus additional indices (and thus one or more additional dimensions in the data tensor).

In this regard, for example, a die or chip j of a wafer i can be represented by a vector having a sequence of measurement values (for example a sequence of passed tests, for example represented by a first binary value "0"), wherein a "failed" test (for example represented by a second binary value "1") can be indicated in the vector in the sequence of "passed" tests, and that can no longer contain a "subsequent" test or a subsequent measurement, which results in missing values in the vector.

Some examples of such vectors are indicated below:
$X_{ij}=(0, \ldots, 0)$: all tests "passed"
$X_{ij}=(1, -, \ldots, -)$: first test "failed"

$X_{ij}$=(0, ..., 0, 1): last test "failed"

$X_{ij}$=(0, ..., 0, 1, -, ..., -): general form: "stop at first failed test" ("stop-at-first-fail")

Figure 5:
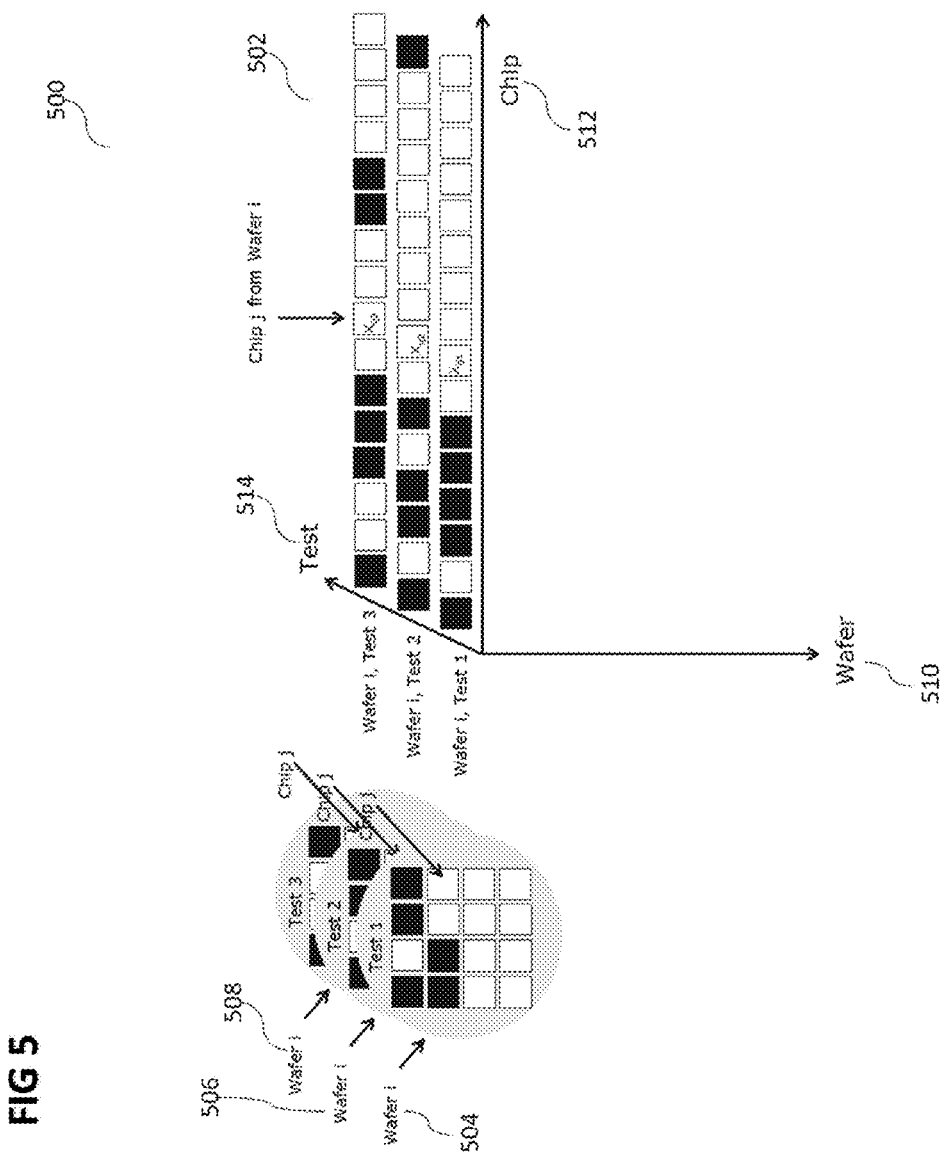
FIG. 5 shows a more detailed illustration of a data tensor for elucidating a blind data separation in accordance with various embodiments.

FIG. 5 shows a more detailed illustration 500 of the structure of the data tensor 502 in accordance with various embodiments.

The left-hand side of FIG. 5 illustrates a wafer i (having the respective chips j) for three different tests, i.e. for example the wafer i which was subjected to a first test (generally a first measurement) (designated by reference sign 504), the wafer i which was subjected to a second test (generally a second measurement) (designated by reference sign 506), and the wafer i which was subjected to a third test (generally a third measurement) (designated by reference sign 508). In the data tensor 502 in FIG. 5, the measurement values $X_{ijt}$ (for example test results) of the chips j of a wafer i are represented in a respective row t, wherein the data tensor 502 represents the different wafers i in a first dimension 510, represents the different chips j of the respective wafers i in a second dimension 512 and represents the different measurements, for example tests, in a third dimension 514.

In various embodiments, the automated computer-aided blind source separation is used for decomposing a number of measurement data or test data, for example wafer measurement data or wafer test data, into basis components which relate to possible original causes and thus into deviation patterns which relate to possible deviations from predefined setpoint values or errors for tensor measurement values or tensor test results.

This means, for example, that without any restriction of general validity it is assumed
that each wafer i has a plurality of dies j or chips j;
that each die j or chip j is subjected to a sequence of measurement processes and/or test processes;
that each deviation from setpoint measurement values or each failed test has a mixture, to put it another way a (for example additive) combination of a plurality of individual source causes k (for example harmful influences k).

Various embodiments illustratively provide a tensor factorization (for example with incomplete measurement data or test data) into hidden (initially not necessarily known in the context of the method) basis patterns $H_{kjt}$ (also designated as deviation patterns, for example fault patterns), linked to source causes k (for example harmful influences k) and weight values $W_{ik}$ linked to a respective activation.

FIG. 1 shows an illustration 100 for elucidating a blind data separation in accordance with various embodiments.

FIG. 1 shows a multiplicity of wafers i 102 wherein each wafer i 102 has a multiplicity of dies j 104 or chips j 104 which are assigned measurement values or test values. The measurement values or test values can have a binary value ("0" or "1") which can indicate, for example, whether or not a die j 104 or chip j 104 has passed a respective test (also designated as test process) t, or some other arbitrary value (not necessarily an integer) which indicates, for example, a measurement value determined in each case for the die j 104 or chip j 104 in a respective measurement process t or which indicates how well the respective die j or chip j 104 passed a respective test t or by how narrow or significant a margin the respective die j 104 or chip j 104 failed a respective test t.

FIG. 1 shows merely by way of example some fault-free dies j 106 or chips j 106 or dies j 108 or chips j 108 classified as deviating (for example dies j 108 or chips j 108 which failed a test t).

The wafers i 102 illustrated on the right-hand side of FIG. 1 represent the actual measurement values or test results, and the wafers 110 shown on the left-hand side of FIG. 1 represent the deviation patterns 112 (for example fault patterns 112) which are determined by the blind source separation and which are linked to a respective source cause k (for example harmful influence k). The weight values $W_{ik}$ 114 linked to a respective activation are furthermore illustrated.

Illustratively, hidden elementary deviation patterns H are represented, which are mixed individually, in a manner weighted with the weights W and cause the observed (measurement values or test data) data X.

Figure 2:
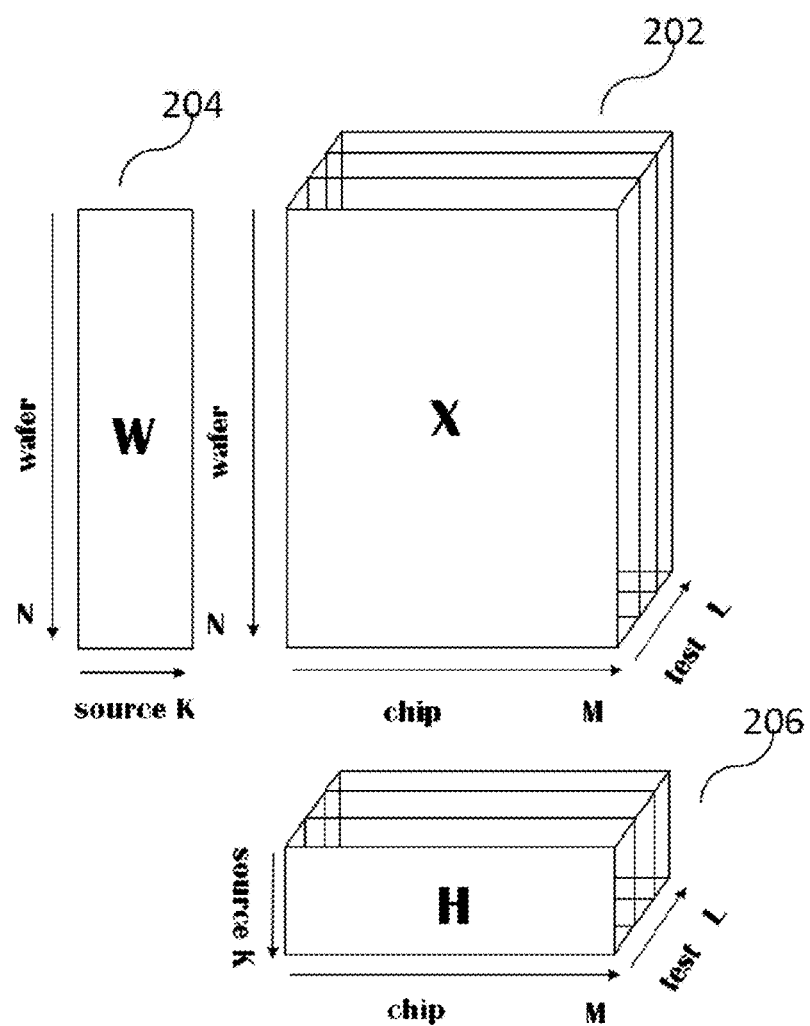
FIG. 2 shows a data tensor for illustrating a blind data separation in accordance with various embodiments.

FIG. 2 shows a data tensor 202 for illustrating a blind data separation in accordance with various embodiments.

Without any restriction of general validity, the following is assumed:
N denotes the number of wafers;
M denotes the number of dies or chips per wafer;
L denotes the number of different measurement processes or test processes; and
K denotes the number of hidden deviation patterns, for example fault patterns.

The N×M×L data tensor 202 of measurement data X or test data X is to be decomposed into a product of a (for example non-negative) N×K weight matrix W 204 (N wafers×K deviation patterns, also designated as causes or sources) and a (for example non-negative) K×M×L tensor 206 (for example K deviation patterns×M dies or chips×L measurement processes or test processes) of hidden basis components H. The N×M×L data tensor 202 can be a binary N×M×L data tensor 202, but it can also contain non-binary values, depending on the requirement. The N×M×L data tensor 202 can be a non-negative N×M×L data tensor 202.

As a result, in various embodiments, information for example about which test a chip 102 failed (or how (clearly) a chip 102 passed or failed a test) is included in the analysis. This enables a considerably more detailed and thus more accurate deviation cause analysis (for example fault cause analysis).

In various embodiments, a method of non-negative tensor factorization is used as blind source separation, wherein the data tensor 202 contains the measurement values X or test data X.

The measurement values X or test data X are contained in the three-dimensional data tensor 202, wherein the first index i identifies the wafer 102, wherein the second index j identifies the die or chip, and wherein the third index t identifies the measurement process or test process.

Each data tensor element $X_{ijt}$ can assume for example one of the following values (it should be noted that these values can be correspondingly adapted for example when taking account of measurement values and thus of non-binary values which a data tensor element $X_{ijt}$ can assume):
$X_{ijt}$=1 (die j or chip j on wafer i has failed test process t);
$X_{ijt}$=0 (die j or chip j on wafer i has passed test process t);
$X_{ijt}$=missing (test result t is missing for die j or chip j on wafer i)

The tensor elements $H_{kjt}$ contained in the tensor 206 describing the hidden deviation patterns (e.g. fault patterns) are likewise arranged in three dimensions, wherein the value of a respective tensor element $H_{kjt}$ indicates a reference to the probability that the die j or the chip j has failed the test process t on account of a fault cause k, for example.

An entry $W_{ik} \geq 0$ of the weight matrix W represents the activity of, for example, a fault cause k on the wafer i.

The "passed/failed" probabilities of the die j or chip j on wafer i in test process t in accordance with a set of K mutually (statistically) independent deviation causes, for example fault causes, can be modelled as follows in various embodiments:

$$P(X_{ijt}=0|S_k) = \exp(-W_{ij}H_{kjt}) \quad (1)$$

$$P(X_{ijt}=1|S_k) = 1-\exp(-W_{ij}H_{kjt}) \quad (2)$$

$$P(X_{ijt}=0|S_1,\ldots,S_k) = \Pi_{k=1}^{K}\exp(-W_{ik}H_{kjt}) = \exp(-\Sigma_{k=1}^{K}W_{ik}H_{kjt}) \quad (3)$$

$$P(X_{ijt}=1|S_1,\ldots,S_k) = 1-\exp(-\Sigma_{k=1}^{K}W_{ik}H_{kjt}) \quad (4)$$

Equation (1) describes the probability of the die j or chip j on wafer i passing the test process t under the condition that the deviation cause k, for example the fault cause k, is active.

Equation (2) describes the probability of the die j or chip j on wafer i failing the test process t under the condition that the deviation cause k, for example the fault cause k, is active.

Equation (3) describes the probability of the die j or chip j on wafer i passing the test process t under the condition that K mutually independent deviation causes, for example fault causes, are active.

Equation (4) describes the probability of the die j or chip j on wafer i failing the test process t under the condition that K mutually independent deviation causes, for example fault causes, are active.

In order to estimate the optimum factors W and H from the data X, a maximum likelihood optimization method is carried out in various embodiments.

In various embodiments, a log likelihood function (for example a cost function) $LL_{binNTF}$ has the following structure (it should be pointed out that any other cost function of a non-negative tensor factorization method can be provided in alternative embodiments):

$$LL_{biNTF} = \Sigma_{i=1}^{N}\Sigma_{j=1}^{M}\Sigma_{t=1}^{L}\{g_{ijt}X_{ijt}\ln(1-\exp(-[WH]_{ijt})) - [WH]_{ijt} + g_{ijt}X_{ijt}[WH]_{ijt}\} \quad (5)$$

In various embodiments, this cost function is optimized in an iterative method taking account of the non-negativity prerequisite W, H>=0 (for each entry of the matrix or tensor).

The parameters $g_{ijt}$ are optional additional parameters which can be provided for weighting individual determined test data in order to improve the optimization method. In this regard, for example, prior knowledge about the reliability of a test process t, by such a parameter, can be taken into account in the context of the optimization.

As an alternative to maximizing the log likelihood function, in alternative embodiments it is likewise possible to minimize a cost function, which rates the difference between the data X and an approximation of the model parameters in order to determine the desired solution W and H for the determined data X.

A family of alternative cost functions is given by:

$$E_{pqr}(X,W,H) = \Sigma_{i=1}^{N}(\Sigma_{j=1}^{M}(\Sigma_{t=1}^{L}g_{ijt}|X_{ijt} - f_{ijt}(W,H)|^p)^q)^r, p,q,r > 0 \quad (6)$$

where e.g. $f_{ijt}(W,H) = 1-\exp(-[WH]_{ijt})$

Setting the parameters $g_{ijt}=1$, p=2, q=1, and r=1 and $f_{ijt}(W,H)=[WH]_{ijt}$ results in a quadratic cost function (quadratic Euclidean distance) between the determined data X and their approximation, expressed by the matrix W and the tensor H.

An adaptation or alteration of the weights $g_{ijt}$ enables an individual treatment of the different test presses (generally of the different measurement processes or test processes) for example with regard to their reliability, as was explained above. The parameters p, q, r serve for being able to concentrate on specific properties of the desired solutions, for example by concentrating on an entire wafer, a selected group of dies or chips, or test processes (generally measurement processes).

It should be noted that the summations over i, j, and t can be permuted.

A different family of cost functions is given by the so-called Kullbach-Leibler divergence between the determined data X and the model approximation W, H as follows:

$$gKL(X,W,H) = \Sigma_{i,j,t}g_{ijt}\left(X_{ijt}\ln\left[\frac{X_{ijt}}{1-e^{-[WH]_{ijt}}}\right] - [X_{ijt} - (1-e^{[WH]_{ijt}})]^r\right), \quad (7)$$

where r>0.

The cost function, generally the likelihood function is optimized in a manner known per se by arbitrary suitable methods, for example by an alternating gradient ascent method.

In the alternating gradient ascent method, it is possible to use the following basis gradient ascent scheme, for example:

$$W_{ik} \leftarrow W_{ik} + \mu_W \frac{\partial LL}{\partial W_{ik}}, \quad (8)$$

$$H_{kjt} \leftarrow H_{kjt} + \mu_H \frac{\partial LL}{\partial H_{kjt}}, \quad (9)$$

In the context of the iterative method, care should be taken to ensure that the left sides of equations (8) and (9) do not become negative. In various embodiments, this is achieved by suitable choice of the step size parameters $\mu_W$ and $\mu_H$.

An alternative optimization method for application to the cost function respectively chosen is the application of the so-called multiplicative updating rules. This optimization method does not require separate choice or control of step size parameters.

The respective optimization method can be ended after a predefinable termination criterion has been satisfied, for example after a predefined number of iterations carried out;
upon obtaining a predefined convergence criterion, for example upon obtaining an only (predefinably) slight change in the respective values $W_{ik}$, $H_{kjt}$ between two or more successive iterations; or
some other suitable termination criterion.

The result of the optimization method is an optimized set of values $W_{ik}$, $H_{kjt}$ and the deviation patterns sought are thereby determined.

Independently of the cost function or likelihood function actually used, in various embodiments, as was explained above, it can happen that the data tensor 202 is not completely filled with values, to put it another way the data tensor 202 can lack some values of the measurement data or test data, for example on account of a "stop-at-first-fail" procedure.

In various embodiments, this case can be combated by an expectation maximization.

It is assumed in this case that the data tensor X 202 is not completely filled with values $X_{ijt}$.

The EM method is carried out in the following manner in the context of the non-negative tensor factorization:

1. Initialization Step:

The entries $W_{ik}$ of the weight matrix W 204 and the values $H_{kjt}$ of the tensor H 206 are initialized with predefinable suitable values (they can for example also be initialized simply with a standard initialization value, such as "0" or "1", for example).

The following processes 2. and 3. are carried out repeatedly until a predefinable termination criterion or convergence criterion is satisfied.

2. E-Step (Expectation):

The expectation values of the values $X_{ijt}$ supplemented for the "missing" values are determined under the assumption that the expectation values of the incoming values correspond to those calculated in the maximization step. In the first iteration, these could also be estimated or randomly allocated.

This can be carried out for example in the following manner:

$$P(X_{ijt}=1)=1-\exp(-[WH]_{ijt}) \text{ or}$$

$$X_{ijt}=1-\exp(-[WH]_{ijt}).$$

3. M-Step (Maximization):

The values $W_{ik}$ of the weight matrix W 204 and $H_{kjt}$ of the tensor H 206 are updated by the likelihood function being maximized (now all with the completely "filled" data tensor 202 $X_{ijt}$), wherein $W_{ik}, H_{kjt} \geq 0$.

In various embodiments, the M-step is an extension of a (for example binary) non-negative matrix factorization to form a (for example binary) non-negative tensor factorization for completing data, which constitutes iteratively solving the likelihood function (for example the log likelihood function $LL_{binNTF}$ described above). It should be noted that it may be numerically advantageous if the determined data and the "missing" values input are weighted differently during the optimization, for example by the weight parameters $g_{ijt}$ being altered.

Figure 3:
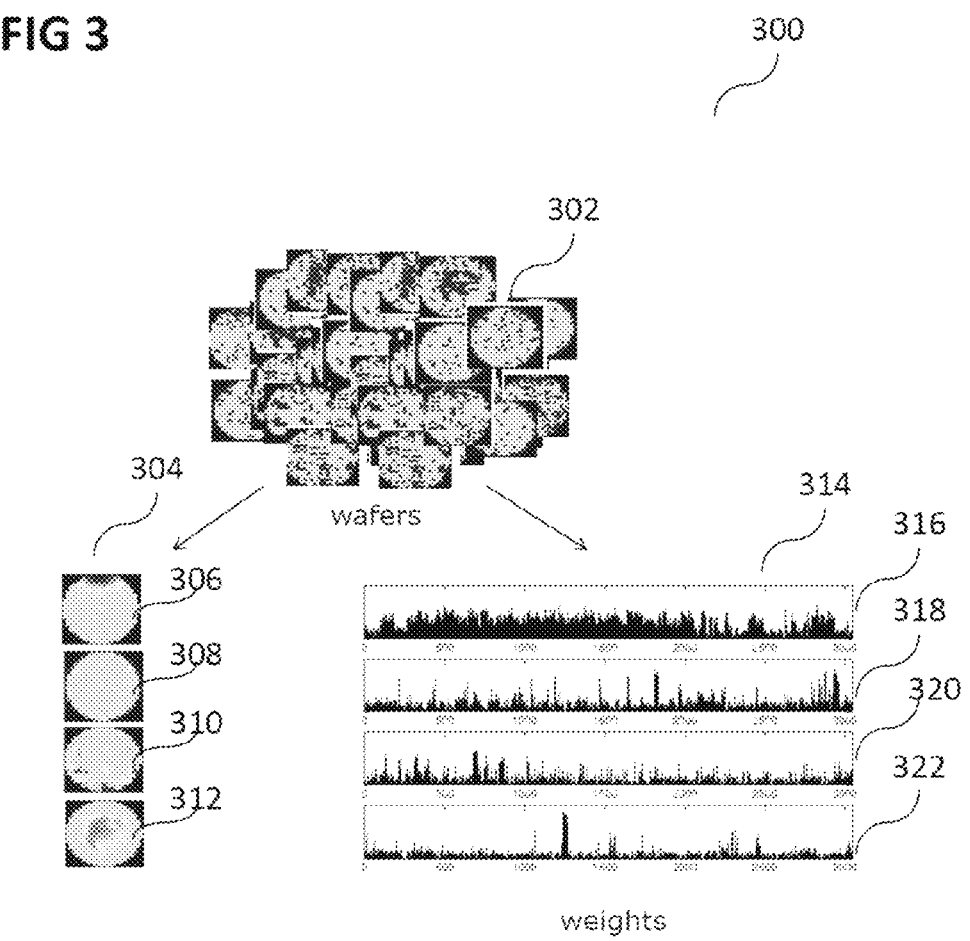
FIG. 3 shows an illustration for elucidating a blind data separation in accordance with various embodiments.

FIG. 3 shows an illustration 300 for elucidating a blind data separation in accordance with various embodiments.

FIG. 3 illustrates a multiplicity of wafers 302, for the dies of which a multiplicity of measurement processes and/or test processes (here only a respective test result for the sake of clarity) were carried out, and the measurement values and/or test data correspondingly assigned to the dies are stored for example in the form of the data tensor 202, as illustrated in FIG. 2.

The result of the method described above is firstly a number of K deviation patterns (for example fault patterns) 304, for example a first deviation pattern (for example fault pattern) 306, a second deviation pattern (for example fault pattern) 308, a third deviation pattern (for example fault pattern) 310, and/or a fourth deviation pattern (for example fault pattern) 312. Furthermore, the weights 314 assigned in each case to a respective deviation pattern (for example fault pattern) and values for each wafer, for example the number of "faulty" dies or chips which failed a specific test, arise as the result. A first partial weight matrix 316 is assigned to the first deviation pattern (for example fault pattern) 306, a second partial weight matrix 318 is assigned to the second deviation pattern (for example fault pattern) 308, a third partial weight matrix 320 is assigned to the third deviation pattern (for example fault pattern) 310, and/or a fourth partial weight matrix 322 is assigned to the fourth deviation pattern (for example fault pattern) 312.

Figure 4:
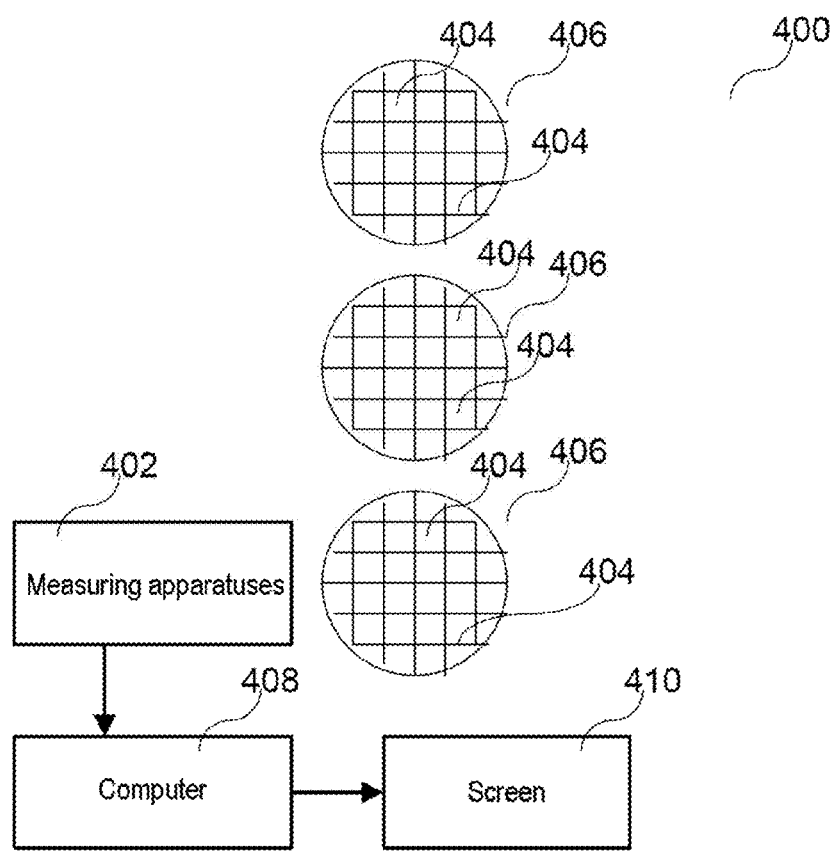
FIG. 4 shows an arrangement with which various embodiments are carried out.

FIG. 4 shows an arrangement 400 with which various embodiments are carried out.

The arrangement 400 includes a multiplicity of measuring apparatuses 402, for example a multiplicity of testers 402, which are represented as a common block 402 in FIG. 4 for the sake of simplicity.

The measuring apparatuses 402, for example the testers 402, carry out measurements or tests on dies 404 or chips 404 of a multiplicity of wafers 406. The measuring apparatuses 402, for example the testers 402, communicate the determined measurement values, for example test data, to a computer 408, for example by a communication connection, for example in a wired or wireless manner. Optionally, the measuring apparatuses 402 can carry out analogue or digital signal processing of the detected measurement signals before the data are sent to the computer 408 and are stored there in a memory of the computer 408. The computer 408 can be designed to carry out the methods described above. Accordingly, the corresponding computer programs can be stored in a memory of the computer 408 and can be executed by a processor. The methods described above can alternatively be implemented in hardware or in hybrid form, i.e. partly in hardware and partly in software.

The determined deviation patterns (for example the multiplicity of deviation patterns 304) and the determined weights 314 can be output to a user by an output apparatus 410 (for example a printer or a screen 410).

The determined variables 304, 314 can be evaluated manually or visually by a user or by a computer-aided deviation analysis system, for example fault analysis system, which is designed to determine probable deviation causes, for example fault causes, on the basis of the determined variables 304, 314.

FIG. 6 shows a flow diagram 600 illustrating a method for the computer-aided determination of deviation patterns during the production and/or testing of a multiplicity of dies, wherein the dies are uniquely identified. The method may include, in 602, determining, for each die of the multiplicity of dies and for at least one measurement process of a plurality of measurement processes which are applied to at least one portion of the dies, a measurement value which was determined in the measurement process for the respective die, and, in 604, carrying out a blind source separation using the measurement values, thereby determining the deviation patterns for the dies.

FIG. 7 shows a flow diagram 700 illustrating a method for the computer-aided determination of at least one deviation cause, for example fault cause of faults during the production and/or testing of a multiplicity of dies, wherein the dies are uniquely identified. The method may include, in 602, determining, for each die of the multiplicity of dies and for at least one measurement process of a plurality of measurement processes which are applied to at least one portion of the dies, a measurement value which was determined in the measurement process for the respective die, and, in 604, carrying out a blind source separation using the measurement values, thereby determining the deviation patterns for the dies. The method may furthermore include, in 702, determining the deviation cause, for example the fault cause, using the deviation patterns determined.

Figure 8:
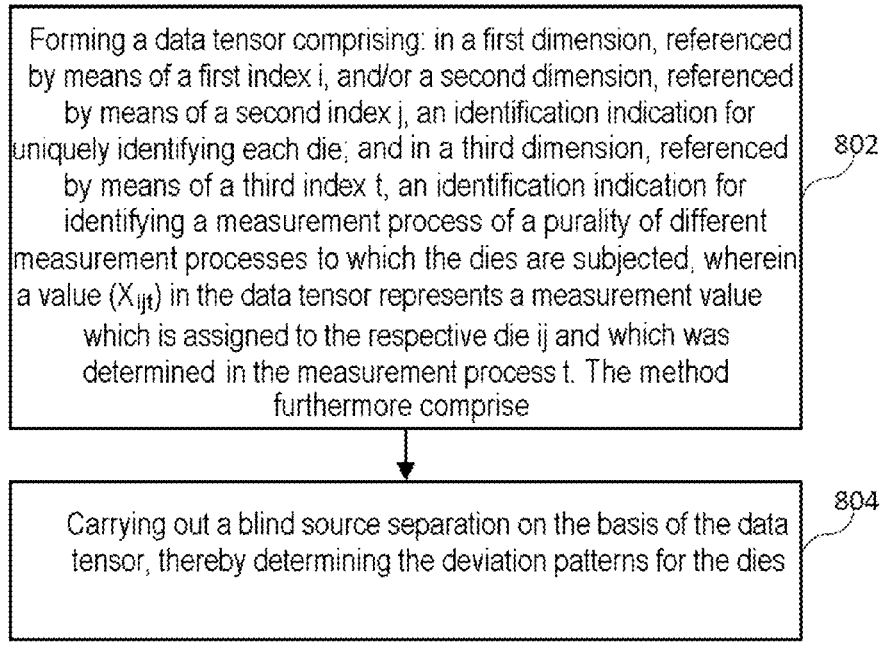
FIG. 8 shows a flow diagram illustrating a method for the computer-aided determination of deviation patterns during the production and/or testing of a multiplicity of dies, wherein the dies are uniquely identified.

FIG. 8 shows a flow diagram 800 illustrating a method for the computer-aided determination of deviation patterns during the production and/or testing of a multiplicity of dies, wherein the dies are uniquely identified. The method may include, in 802, forming a data tensor including: in a first dimension, referenced by a first index i, and/or a second dimension, referenced by a second index j, an identification indication for uniquely identifying each die; and in a third dimension, referenced by a third index t, an identification indication for identifying a measurement process of a plurality of different measurement processes to which the dies are subjected, wherein a value ($X_{ijt}$) in the data tensor represents a measurement value which is assigned to the respective die ij and which was determined in the measurement process t. The method may furthermore include, in 804, carrying out a blind source separation on the basis of the data tensor, thereby determining the deviation patterns for the dies.

FIG. 9 shows a flow diagram 900 illustrating a method for the computer-aided determination of at least one deviation cause, for example at least one fault cause of faults during the production and/or testing of a multiplicity of dies, wherein the dies are uniquely identified. The method may include, in 802, forming a data tensor including: in a first dimension, referenced by a first index i, and/or a second dimension, referenced by a second index j, an identification indication for uniquely identifying each die; and in a third dimension, referenced by a third index t, an identification indication for identifying a measurement process of a plurality of different measurement processes to which the dies are subjected, wherein a value ($X_{ijt}$) in the data tensor represents a measurement value which is assigned to the respective die ij and which was determined in the measurement process t. The method may furthermore include, in 804, carrying out a blind source separation on the basis of the data tensor, thereby determining the deviation patterns for the dies. The method may furthermore include, in 902, determining the deviation cause, for example the fault cause, using the deviation patterns determined.

In one configuration, the multiplicity of dies may include a multiplicity of chips (optionally free of sawing frames, possibly already individual singulated chips).

The dies may include identical or different chips. The dies can also be grouped into a plurality of groups and it is possible to determine measurement values or to carry out tests which relate to a respective group of a plurality of dies or chips.

The wafers can likewise be identical or different. The wafers may include for example semiconductor material, for example silicon, germanium, group III to V materials or other materials, including polymers. In various embodiments, a wafer may include silicon or substantially consist thereof (doped or undoped). In various embodiments, a wafer can be a silicon on insulator (SOI) wafer. Alternatively, a wafer may include any other semiconductor material or essentially consist thereof, for example a semiconductor composite material such as, for example, gallium arsenide (GaAs), indium phosphide (InP), but also any suitable ternary semiconductor composite material or quaternary semiconductor composite material such as indium gallium arsenide (InGaAs), for example.

The plurality of measurement processes may include a plurality of test processes which are applied to at least one portion of the dies, and determining a measurement value for each die of the multiplicity of dies and for at least one measurement process of a plurality of measurement processes may include determining, for each die of the multiplicity of dies and for at least one test process of the plurality of test processes, whether or how a respective die has passed or has not passed the test process.

Furthermore, carrying out the blind source separation may include carrying out a non-negative tensor factorization, wherein the tensor contains the measurement values, wherein carrying out a non-negative tensor factorization may include carrying out a maximum likelihood optimization method.

For the case that no measurement value is determined for at least one die for at least one measurement process of the plurality of measurement processes, the measurement value can be replaced (illustratively supplemented or filled up) by a value which is determined by an expectation maximization method (EM method) and this value can be used in the context of the blind source separation.

Each die can be assigned an identification indication which uniquely identifies the die within a wafer containing the die, and also the wafer.

The deviation pattern can be a fault pattern.

In various embodiments, a device for the computer-aided determination of deviation patterns during the production and/or testing of a multiplicity of dies is provided, wherein the dies are uniquely identified. The device may include a processor designed to perform the following method: determining, for each die of the multiplicity of dies and for at least one measurement process of a plurality of measurement processes, a measurement value which was determined in the measurement process for the respective die; and carrying out a blind source separation using the measurement values, thereby determining the deviation patterns for the dies.

In various embodiments, a computer program product for the computer-aided determination of deviation patterns during the production and/or testing of a multiplicity of dies is provided, wherein the dies are uniquely identified. The computer program product, if it is executed by a processor, carries out the following method: determining, for each die of the multiplicity of dies and for at least one measurement process of a plurality of measurement processes, a measurement value which was determined in the measurement process for the respective die; and carrying out a blind source separation using the measurement values, thereby determining the deviation patterns for the dies.

In various embodiments, a method for the computer-aided determination of at least one cause of a determined deviation, for example a fault cause of faults during the production and/or testing of a multiplicity of dies, is provided, wherein the dies are uniquely identified. The method includes: carrying out a method for the computer-aided determination of deviation patterns during the production and/or testing of a multiplicity of dies; and determining the cause of the deviation, for example the fault cause, using the deviation patterns determined, as was described above or will be explained in greater detail below.

In various embodiments, a method for the computer-aided determination of deviation patterns during the production and/or testing of a multiplicity of dies is provided, wherein the dies are uniquely identified. The method includes forming a data tensor including: a first dimension, referenced by a first index i, and/or a second dimension, referenced by a second index j, an identification indication for uniquely identifying each die; and a third dimension, referenced by a third index t (it should be pointed out that generally even further dimensions/indices are also possible and can be provided), an identification indication for identifying a measurement process of a plurality of different measurement processes to which the dies are subjected, wherein a value in the data tensor represents a measurement value which is assigned to the respective die ij and which was determined in the measurement process t. The method furthermore includes carrying out a blind source separation on the basis of the data tensor, thereby determining the deviation patterns for the dies. For example, different groups of tests or measurements (for example at different temperatures) or different groups of wafers (for example in batches) or else defined desired groups of chips on a respective wafer could be provided as further dimensions of the data tensor. Said groups can in each case form for example an additional dimension of the data tensor.

The multiplicity of dies may include a multiplicity of chips.

The plurality of measurement processes may include a plurality of test processes which are applied to at least one portion of the dies, and determining a measurement value for each die of the multiplicity of dies and for at least one measurement process of a plurality of measurement processes may include determining, for each die of the multiplicity of dies and for at least one test process of the plurality of test processes, whether or how a respective die has passed or has not passed the test process.

Furthermore, carrying out the blind source separation may include carrying out a non-negative tensor factorization, wherein the tensor contains the measurement values, wherein carrying out a non-negative tensor factorization may include carrying out a maximum likelihood optimization method.

For the case that no measurement value is determined for at least one die for at least one measurement process of the plurality of measurement processes, the measurement value can be replaced by a value which is determined by an expectation maximization method and this value can be used in the context of the blind source separation.

Each die can be assigned an identification indication which uniquely identifies the die within a wafer containing the die, and also the wafer.

The deviation pattern can be a fault pattern.

In various embodiments, a device for the computer-aided determination of deviation patterns during the production and/or testing of a multiplicity of dies is provided, wherein the dies are uniquely identified. The device may include a processor designed to perform the following method: forming a data tensor including: a first dimension, referenced by a first index i, and/or a second dimension, referenced by a second index j, an identification indication for uniquely identifying each die; and a third dimension, referenced by a third index t, an identification indication for identifying a measurement process of a plurality of different measurement processes to which the dies are subjected, wherein a value in the data tensor represents a measurement value which is assigned to the respective die ij and which was determined in the measurement process t; and carrying out a blind source separation on the basis of the data tensor, thereby determining the deviation patterns for the dies.

In various embodiments, a computer program product for the computer-aided determination of deviation patterns during the production and/or testing of a multiplicity of dies is provided, wherein the dies are uniquely identified. The computer program product, if it is executed by a processor, carries out the following method: forming a data tensor including: a first dimension, referenced by a first index i, and/or a second dimension, referenced by a second index j, an identification indication for uniquely identifying each die; and a third dimension, referenced by a third index t, an identification indication for identifying a measurement process of a plurality of different measurement processes to which the dies are subjected, wherein a value in the data tensor represents a measurement value which is assigned to the respective die ij and which was determined in the measurement process t; and carrying out a blind source separation on the basis of the data tensor, thereby determining the deviation patterns for the dies.

In various embodiments, a method for the computer-aided determination of at least one cause of a deviation, for example a fault cause of faults, during the production and/or testing of a multiplicity of dies is provided, wherein the dies are uniquely identified. The method may include: carrying out a method for the computer-aided determination of deviation patterns during the production and/or testing of a multiplicity of dies, as was described above or will be described below. The method may furthermore include determining the deviation cause using the deviation patterns determined.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method for the determination of at least one deviation cause in dies from determined deviation patterns during at least one of the production or testing of a multiplicity of dies the method comprising:
uniquely identifying each of the multiplicity of dies;
performing a plurality of measurement processes on at least one portion of the dies;
determining, for each die of the multiplicity of dies and for at least one measurement process of the plurality of measurement processes that are applied to the at least one portion of the dies, a measurement value which was determined in the measurement process for the respective die;
carrying out a blind source separation using the measurement values, thereby determining the deviation patterns for the dies; and
determining the at least one deviation cause using the deviation patterns determined.

2. The method of claim 1,
wherein the multiplicity of dies comprises a multiplicity of chips.

3. The method of claim 1,
wherein the plurality of measurement processes comprises a plurality of test processes which are applied to at least one portion of the dies; and
wherein determining a measurement value for each die of the multiplicity of dies and for at least one measurement process of a plurality of measurement processes comprises determining, for each die of the multiplicity of dies and for at least one test process of the plurality of test processes, whether or how a respective die has passed or has not passed the test process.

4. The method of claim 1,
wherein carrying out the blind source separation comprises carrying out a non-negative tensor factorization, wherein the tensor contains the measurement values.

5. The method of claim 4,
wherein carrying out a non-negative tensor factorization comprises carrying out a maximum likelihood optimization method.

6. The method of claim 1,
wherein for the case that no measurement value is determined for at least one die for at least one measurement process of the plurality of measurement processes, the measurement value is replaced by a value which is determined by an expectation maximization method and this value is used in the context of the blind source separation.

7. The method of claim 1,
wherein each die is assigned an identification indication which uniquely identifies the die within a wafer containing the die, and also the wafer.

8. The method of claim 1,
wherein the deviation patterns are fault patterns.

9. A device for the determination of at least one deviation cause in dies from determined deviation patterns during at least one of the production or testing of a multiplicity of dies wherein the device comprises a processor designed to perform the following method:
uniquely identifying each of the multiplicity of dies;
controlling performance of a plurality of measurement processes on at least one portion of the dies;
determining, for each die of the multiplicity of dies and for at least one measurement process of the plurality of measurement processes, a measurement value that was determined in the measurement process for the respective die;
carrying out a blind source separation using the measurement values, thereby determining the deviation patterns for the dies; and
determining the at least one deviation cause using the deviation patterns determined.

10. A non-transitory computer readable medium configured to store instructions for execution by a processor for the determination of at least one deviation cause in dies from determined deviation patterns during at least one of the production or testing of a multiplicity of dies the instructions when executed by the processor, carry out the following method:
uniquely identifying each of the multiplicity of dies;
controlling performance of a plurality of measurement processes on at least one portion of the dies;
determining, for each die of the multiplicity of dies and for at least one measurement process of the plurality of measurement processes, a measurement value which was determined in the measurement process for the respective die;
carrying out a blind source separation using the measurement values, thereby determining the deviation patterns for the dies; and
determining the at least one deviation cause using the deviation patterns determined.

11. A method for correcting at least one deviation cause in dies from determined deviation patterns during at least one of the production or testing of a multiplicity of dies the method comprising:
uniquely identifying each of the multiplicity of dies;
performing a plurality of measurement processes on at least one portion of the dies;
determining, for each die of the multiplicity of dies and for at least one measurement process of the plurality of measurement processes that are applied to the at least one portion of the dies, a measurement value that was determined in the measurement process for the respective die;
carrying out a blind source separation using the measurement values, thereby determining the deviation patterns for the dies;
determining the at least one deviation cause using the deviation patterns determined; and
correcting the at least one deviation cause during production or testing of another multiplicity of dies.

12. A method for the determination of at least one deviation cause in dies from determined deviation patterns during at least one of the production or testing of a multiplicity of dies the method comprising:
uniquely identifying each of the multiplicity of dies;
performing a plurality of measurement processes on at least one portion of the dies;
forming a data tensor comprising:
in a first dimension, referenced by at least one of a first index i or a second dimension, referenced by a second index j, an identification indication for uniquely identifying each die; and
in a third dimension, referenced by a third index t, an identification indication for identifying a measurement process of the plurality of measurement processes to which the dies are subjected,
wherein a value ($X_{ijt}$) in the data tensor represents a measurement value which is assigned to the respective die ij and which was determined in the measurement process t;
carrying out a blind source separation on the basis of the data tensor, thereby determining the deviation patterns for the dies; and
determining the at least one deviation cause using the deviation patterns determined.

13. The method of claim 12,
wherein the multiplicity of dies comprises a multiplicity of chips.

14. The method of claim 12,
wherein the plurality of measurement processes comprises a plurality of test processes; and
wherein determining a measurement value for each die of the multiplicity of dies and for at least one measurement process of a plurality of measurement processes comprises determining, for each die of the multiplicity of dies and for at least one test process of the plurality of test processes, whether or how a respective die has passed or has not passed the test process.

15. The method of claim 12,
wherein carrying out the blind source separation comprises carrying out a non-negative tensor factorization, wherein the tensor contains the measurement values.

16. The method of claim 15,
wherein carrying out a non-negative tensor factorization comprises carrying out a maximum likelihood optimization method.

17. The method of claim 12,
wherein for the case that no measurement value is determined for a die for at least one measurement process of the plurality of measurement processes, the measurement value is replaced by a value which is determined by means of an expectation maximization method and this value is used in the context of the blind source separation.

18. The method of claim 12,
wherein each die is assigned an identification indication which uniquely identifies the die within a wafer containing the die, and also the wafer.

19. The method of claim 12,
wherein the deviation patterns are fault patterns.

20. A device for the determination of at least one deviation cause in dies from determined deviation patterns during at least one of the production or testing of a multiplicity of dies wherein the device comprises a processor designed to perform the following method:

uniquely identifying each of the multiplicity of dies;
controlling performance of a plurality of measurement processes on at least one portion of the dies;
forming a data tensor comprising:
  in a first dimension, referenced by at least one of a first index i or a second dimension, referenced by a second index j, an identification indication for uniquely identifying each die; and
  in a third dimension, referenced by a third index t, an identification indication for identifying a measurement process of a plurality of different measurement processes to which the dies are subjected,
  wherein a value ($X_{ijt}$) in the data tensor represents a measurement value which is assigned to the respective die ij and which was determined in the measurement process t;
carrying out a blind source separation on the basis of the data tensor, thereby determining the deviation patterns for the dies; and
determining the at least one deviation cause using the deviation patterns determined.

21. A non-transitory computer readable medium configured to store instructions for execution by a processor for the determination of at least one deviation cause in dies from determined deviation patterns during the production and/or testing of a multiplicity of dies the instructions when executed by the processor, carry out the following method:
uniquely identifying each of the multiplicity of dies;
controlling performance of a plurality of measurement processes on at least one portion of the dies;
forming a data tensor comprising:
  in a first dimension, referenced by at least one of a first index i or a second dimension, referenced by a second index j, an identification indication for uniquely identifying each die; and
  in a third dimension, referenced by a third index t, an identification indication for identifying a measurement process of a plurality of different measurement processes to which the dies are subjected,
  wherein a value ($X_{ijt}$) in the data tensor represents a measurement value which is assigned to the respective die ij and which was determined in the measurement process t;
carrying out a blind source separation on the basis of the data tensor, thereby determining the deviation patterns for the dies; and
determining the at least one deviation cause using the deviation patterns determined.

22. A method for correcting at least one deviation cause in dies from determined deviation patterns during at least one of the production or testing of a multiplicity of dies the method comprising:
uniquely identifying each of the multiplicity of dies;
performing a plurality of measurement processes on at least one portion of the dies;
forming a data tensor comprising:
in a first dimension, referenced by at least one of a first index i or a second dimension, referenced by a second index j, an identification indication for uniquely identifying each die; and
in a third dimension, referenced by a third index t, an identification indication for identifying a measurement process of a plurality of different measurement processes to which the dies are subjected,
wherein a value ($X_{ijt}$) in the data tensor represents a measurement value which is assigned to the respective die ij and which was determined in the measurement process t;
carrying out a blind source separation on the basis of the data tensor, thereby determining the deviation patterns for the dies;
determining the at least one deviation cause using the deviation patterns determined; and
correcting the at least one deviation cause during production or testing of another multiplicity of dies.

* * * * *